(12) United States Patent
Terakawa

(10) Patent No.: US 9,962,070 B2
(45) Date of Patent: May 8, 2018

(54) ENDOSCOPE SYSTEM, PROCESSOR DEVICE, AND METHOD FOR OPERATING ENDOSCOPE SYSTEM

(71) Applicant: FUJIFILM Corporation, Tokyo (JP)

(72) Inventor: Yuki Terakawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 890 days.

(21) Appl. No.: 14/471,154

(22) Filed: Aug. 28, 2014

(65) Prior Publication Data
US 2015/0094538 A1 Apr. 2, 2015

(30) Foreign Application Priority Data

Sep. 27, 2013 (JP) .................................. 2013-201273

(51) Int. Cl.
*A61B 1/313* (2006.01)
*A61B 1/06* (2006.01)
*A61B 1/00* (2006.01)

(52) U.S. Cl.
CPC ........ *A61B 1/3137* (2013.01); *A61B 1/00009* (2013.01); *A61B 1/0638* (2013.01)

(58) Field of Classification Search
CPC ....... A61B 1/06; A61B 1/0638; A61B 1/0646; A61B 1/0653; A61B 1/043; A61B 1/00004; A61B 1/00009; A61B 1/0661; A61B 5/0059; A61B 5/0071; A61B 5/489
USPC ........ 600/109, 160, 177, 178, 180, 181, 476
See application file for complete search history.

(56) References Cited

U.S. PATENT DOCUMENTS

| 8,216,126 | B2 | 7/2012 | Gono | |
|---|---|---|---|---|
| 2003/0071895 | A1* | 4/2003 | Higuchi | H04N 7/183 348/65 |
| 2007/0024946 | A1* | 2/2007 | Panasyuk | A61B 5/0059 359/253 |
| 2007/0225553 | A1* | 9/2007 | Shahidi | A61B 5/064 600/103 |
| 2011/0042580 | A1* | 2/2011 | Wilson | G01N 21/6456 250/458.1 |

(Continued)

FOREIGN PATENT DOCUMENTS

JP 4709606 B2 6/2011

*Primary Examiner* — Matthew J Kasztejna
*Assistant Examiner* — William Chou
(74) *Attorney, Agent, or Firm* — Birch, Stewart, Kolasch & Birch, LLP

(57) ABSTRACT

Violet light and blue light is applied sequentially to an object. In a wavelength range (380-440 nm) of the violet light, each of reflectances of most-superficial and superficial blood vessels is lower than reflectance of middle-layer blood vessels. In a wavelength range (440-480 nm) of the blue light, the reflectance of the middle-layer blood vessels is lower than those of the most-superficial and superficial blood vessels. Brightness of mucous membrane in a normalized first signal obtained under the violet light is equivalent to that in a normalized second signal obtained under the blue light. A subtraction image is obtained by subtraction between the normalized first and second signals, and superimposed on the first signal. A special image, in which the most-superficial and superficial blood vessels correspond to falling edges and the middle-layer blood vessels correspond to rising edges and the blood vessels are distinguished from each other, is produced.

13 Claims, 16 Drawing Sheets

(56) References Cited

U.S. PATENT DOCUMENTS

2011/0077462 A1\* 3/2011 Saitou .................. A61B 1/0638
                                                     600/109
2012/0197076 A1\* 8/2012 Minetoma .......... A61B 1/00009
                                                     600/109

\* cited by examiner

FIG. 13
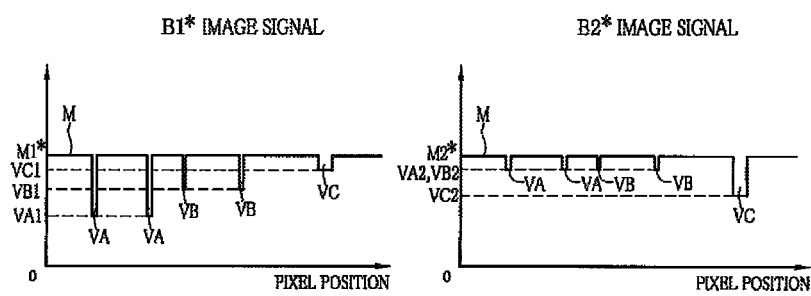
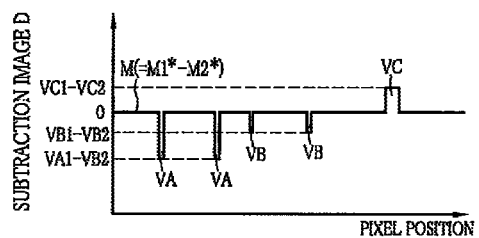
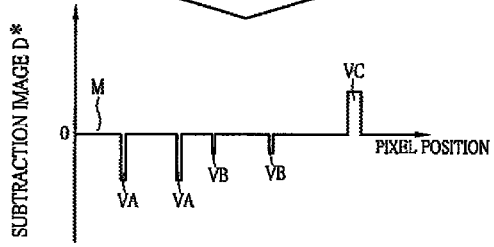

B1 IMAGE SIGNAL

SUPER-
FICIAL
BLOOD
VESSELS
VB

MIDDLE-
LAYER
BLOOD
VESSELS
VC

T

B2 IMAGE SIGNAL

SUPER-
FICIAL
BLOOD
VESSELS
VB

MIDDLE-
LAYER
BLOOD
VESSELS
VC

T

SUBTRACTION IMAGE D

SPECIAL IMAGE

ENDOSCOPE SYSTEM, PROCESSOR DEVICE, AND METHOD FOR OPERATING ENDOSCOPE SYSTEM

CROSS-REFERENCE TO RELATED APPLICATIONS

The present application claims priority under 35 U.S.C. § 119 to Japanese Patent Application No. 2013-201273, filed Sep. 27, 2013. The above application is hereby expressly incorporated by reference, in its entirety, into the present application.

BACKGROUND OF THE INVENTION

1. Field of the Invention

The present invention relates to an endoscope system, a processor device, and a method for operating an endoscope system, capable of enhancing tissue structure such as blood vessels with the use of narrowband light in observation.

2. Description Related to the Prior Art

In a medical field, diagnosis using an endoscope system, which comprises a light source device, an endoscope device, and a processor device, is commonly performed. The diagnosis using the endoscope system includes normal observation, in which broadband light such as white light is used to observe an observation object in its entirety, and narrowband light observation, in which narrowband light of specific wavelengths is used to enhance tissue structure such as blood vessels and ductal structure.

In the narrowband light observation, blue narrowband light is used to enhance superficial blood vessels located in superficial tissue of the observation object. In addition, green narrowband light is used to enhance middle-layer blood vessels located in tissue in a middle layer of the observation object. A blue image signal, which is obtained by imaging the observation object under the blue narrowband light, is assigned to B and G channels of a monitor and a green image signal, which is obtained by imaging the observation object under the green narrowband light, is assigned to an R channel of the monitor (for example, see U.S. Pat. No. 8,216,126 corresponding to Japanese Pat. No. 4709606). Thereby, the superficial blood vessels and the middle-layer blood vessels are displayed in different colors. This makes it easy for a doctor to distinguish between the blood vessels in different layers.

It is generally known that human eyes have high sensitivity to differences in brightness (intensity) in an image, but low sensitivity to differences in color. In a case where the superficial and middle-layer blood vessels are displayed in different colors, the difference in depth between the superficial and middle-layer blood vessels may not be perceived accurately. For this reason, it is desirable to display the superficial and middle-layer blood vessels, which differ from each other in depth, with different brightness instead of different colors.

SUMMARY OF THE INVENTION

An object of the present invention is to provide an endoscope system, a processor device, and a method for operating an endoscope system, capable of displaying blood vessels of different depths, such as superficial and middle-layer blood vessels, with different brightness such that the depths of the blood vessels are distinguished from each other.

In order to achieve the above and other objects, the endoscope system of the present invention comprises a light source unit, an image sensor, a normalizer, a subtraction-image generator, and an image composition unit. The light source unit sequentially applies first illumination light and second illumination light to an observation object. The first illumination light has a wavelength range in which a reflectance of a first blood vessel located at a specific depth is smaller than a reflectance of a second blood vessel located at a depth deeper than the specific depth. The second illumination light has a wavelength range in which the reflectance of the first blood vessel is greater than the reflectance of the second blood vessel. The image sensor images the observation object under the first illumination light and thereby outputs a first image. The image sensor images the observation object under the second illumination light and thereby outputs a second image. The normalizer normalizes the first image and the second image to make brightness of mucous membrane of the observation object in the first image equivalent to brightness of the mucous membrane of the observation object in the second image. The subtraction-image generator produces a subtraction image through a subtraction process between normalized first and second images. The image composition unit produces a special image through superimposing the subtraction image on at least one of the first and second images. In the special image, one of the first and second blood vessels corresponds to a falling edge with a value smaller than a value of the mucous membrane, and the other of the first and second blood vessels corresponds to a rising edge with a value greater than the value of the mucous membrane.

It is preferable that the first and second blood vessels correspond to falling edges in the first or second image. It is preferable that the subtraction-image generator produces the subtraction image in which the first blood vessel corresponds to a falling edge and the second blood vessel corresponds to a rising edge. The image composition unit adds a value of the first blood vessel which corresponds to the falling edge in the subtraction image to a value of the first blood vessel which corresponds the falling edge in the first or second image, and adds a value of the second blood vessel which corresponds to the rising edge in the subtraction image to a value of the second blood vessel which corresponds to the falling edge in the first or second image, and thereby produces the special image in which the first blood vessel corresponds to the falling edge and the second blood vessel corresponds to the rising edge.

It is preferable that a value of the mucous membrane in the subtraction image is "0". It is preferable that the normalizer obtains pixel values of the mucous membrane at the same positions in the first and second images, respectively, and normalizes the first and second images based on the pixel values of the mucous membrane. It is preferable that the normalizer normalizes the first and second images based on the pixel values of the mucous membrane, and the pixel values of the mucous membrane are adjusted in accordance with an amount of the first or second illumination light. It is preferable that the subtraction image is multiplied by an adjustment factor to make one of the first and second blood vessels correspond to the rising edge in the special image.

It is preferable that a reflectance of a third blood vessel, which is located shallower than the first blood vessel, is smaller than the reflectance of the first blood vessel in the wavelength range of the first illumination light. The contrast of the third blood vessel is greater than contrast of the first blood vessel in the special image. It is preferable that the first to third blood vessels correspond to falling edges in the first or second image. It is preferable that the subtraction-image generator produces the subtraction image in which the first and third blood vessels correspond to falling edges and the second blood vessel corresponds to a rising edge. It is preferable that the image composition unit adds a value of the first blood vessel which corresponds to the falling edge in the subtraction image to a value of the first blood vessel which corresponds to the falling edge in the first or second image, and adds a value of the third blood vessel which corresponds to the falling edge in the subtraction image to a value of the third blood vessel which corresponds to the falling edge in the first or second image, and thereby produces the special image in which the first and third blood vessels correspond to falling edges.

It is preferable that the first illumination light has the wavelength range of 380 to 440 nm, and the second illumination light has the wavelength range of 440 to 480 nm. It is preferable that the light source unit has a first LED for emitting the first illumination light and a second LED for emitting the second illumination light.

The processor device of an endoscope system according to the present invention comprises a receiver, a normalizer, a subtraction-image generator, and an image composition unit. The receiver receives the first and second images. The normalizer normalizes the first and second images to make brightness of mucous membrane of the observation object in the first image equivalent to brightness of the mucous membrane of the observation object in the second image. The subtraction-image generator obtains a subtraction image through a subtraction process between normalized first and second images. The image composition unit produces a special image through superimposing the subtraction image on at least one of the first and second images. In the special image, one of the first and second blood vessels corresponds to a falling edge with a value smaller than a value of the mucous membrane, and the other of the first and second blood vessels corresponds to a rising edge with a value greater than the value of the mucous membrane. The endoscope system comprises a light source unit and an image sensor. The light source unit sequentially applies first illumination light and second illumination light to an observation object. The first illumination light has a wavelength range in which a reflectance of a first blood vessel located at a specific depth is smaller than a reflectance of a second blood vessel located at a depth deeper than the specific depth. The second illumination light has a wavelength range in which the reflectance of the first blood vessel is greater than the reflectance of the second blood vessel. The image sensor images the observation object under the first illumination light, and thereby outputs a first image. The image sensor images the observation object under the second illumination light, and thereby outputs a second image.

The method for operating an endoscope system according to the present invention comprises a light applying step, an imaging step, a normalizing step, a subtraction image producing step, and a special image producing step. In the light applying step, a light source unit sequentially applies first illumination light and second illumination light to an observation object. The first illumination light has a wavelength range in which a reflectance of a first blood vessel located at a specific depth is smaller than a reflectance of a second blood vessel located at a depth deeper than the specific depth. The second illumination light has a wavelength range in which the reflectance of the first blood vessel is greater than the reflectance of the second blood vessel. In the imaging step, an image sensor images the observation object under the first illumination light and thereby outputs a first image, and images the observation object under the second illumination light and thereby outputs a second image. In the normalizing step, a normalizer normalizes the first and second images to make brightness of mucous membrane of the observation object in the first image equivalent to brightness of the mucous membrane of the observation object in the second image. In the subtraction image producing step, a subtraction-image generator produces a subtraction image through a subtraction process between normalized first and second images. In the special image producing step, an image composition unit produces a special image through superimposing the subtraction image on at least one of the first and second images. In the special image, one of the first and second blood vessels corresponds to a falling edge with a value smaller than a value of the mucous membrane in the special image, and the other of the first and second blood vessels corresponds to a rising edge with a value greater than the value of the mucous membrane in the special image.

According to the present invention, the blood vessels, such as the superficial and middle-layer blood vessels, at different depths are displayed with different brightness such that the depths of the blood vessels are distinguished from each other.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 13 is an explanatory view illustrating a subtraction process based on the B1and B2 image signals;

DESCRIPTION OF THE PREFERRED EMBODIMENTS (First Embodiment)

Figure 1:
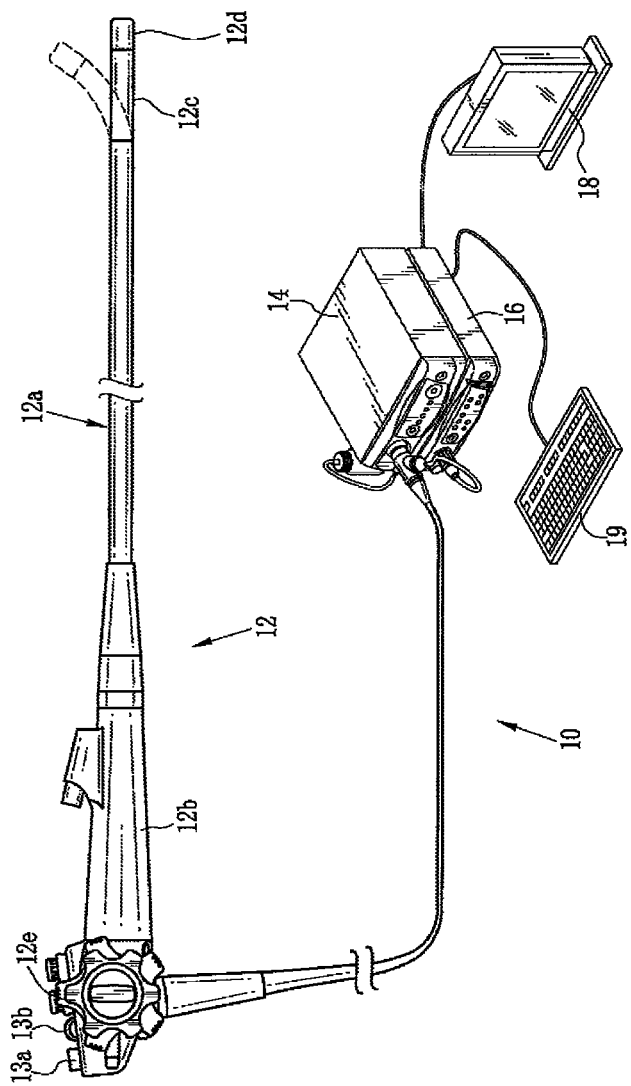
FIG. 1 is an external view of an endoscope system.

As shown in FIG. 1, an endoscope system 10 of a first embodiment comprises an endoscope 12, a light source device 14, a processor device 16, a monitor 18, and a console 19. The endoscope 12 is connected optically to the light source device 14, and electrically to the processor device 16. The endoscope 12 has an insertion section 12a, a control handle 12b, a flexible portion 12c, and a distal portion 12d. The insertion section 12a is inserted into a body cavity. The control handle 12b is provided to a proximal end of the insertion section 12a. The flexible portion 12c and the distal portion 12d are provided on a distal side of the insertion section 12a. The flexible portion 12c is bent by operating an angle knob 12e of the control handle 12b. The distal portion 12d is bent to an intended direction through bending the flexible portion 12c.

The control handle 12b is provided with the angle knob 12e, a mode switch (SW) 13a, and a zoom control unit 13b. The mode SW 13a is used to switch between two operation modes, a normal mode and a special mode. In the normal mode, a normal image is displayed on the monitor 18. The normal image is an image of an observation object captured under normal light such as white light. In a special mode, a special image is displayed on the monitor 18. The special image is an image of an observation object captured under special light of a specific wavelength range. Here, the blood vessels at different depths in the observation object are displayed with different brightness in the special image. The zoom control unit 13b is used for driving a zooming lens 47 (see FIG. 2). The observation object is magnified by moving the zooming lens 47 to a telephoto side.

The processor device 16 is electrically connected to the monitor 18 and the console 19. The monitor 18 outputs and displays image information and the like. The console 19 functions as a UI (user interface), which accepts input operation such as setting a function. Note that an external storage unit (not shown) for recording the image information and the like may be connected to the processor device 16.

Figure 2:
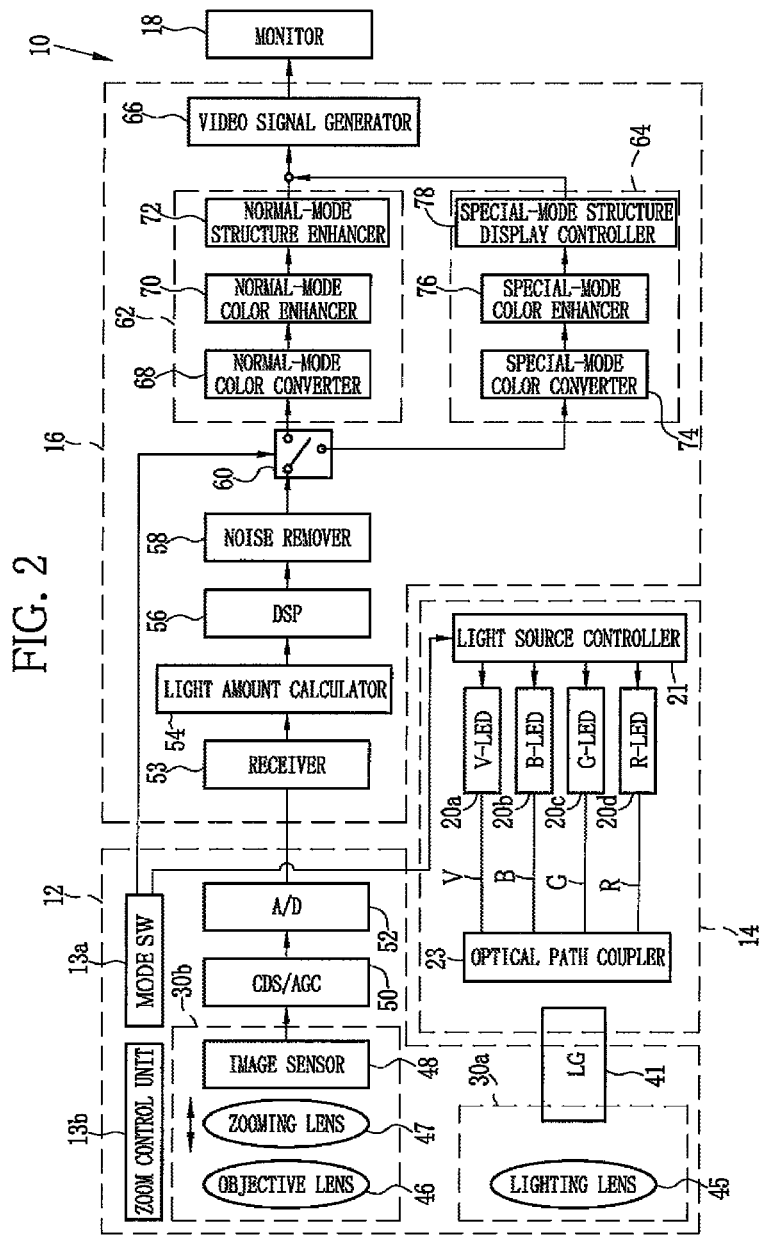
FIG. 2 is a block diagram of the endoscope system of a first embodiment.

As shown in FIG. 2, the light source device 14 comprises a V-LED (violet light emitting diode) 20a, a B-LED (blue light emitting diode) 20b, a G-LED (green light emitting diode) 20c, an R-LED (red light emitting diode) 20d, a light source controller 21 for controlling the drive of the LEDs of the four colors, and an optical path coupler 23. The optical path coupler 23 couples optical paths of light from the LEDs 20a to 20d of the four colors. The light coupled through the optical path coupler 23 is applied to the observation object through a light guide 41 and a lighting lens 45. The light guide 41 extends in the insertion section 12a. Note that an LD (Laser Diode) may be used instead of the LED.

The V-LED 20a generates violet light V with the center wavelength of 400-410 nm and the wavelength range of 380 to 440 nm. The B-LED 20b generates blue light B with the center wavelength of 450-470 nm and the wavelength range of 440 to 480 nm. The G-LED 20c generates normally-distributed green light G with the wavelength range of 480 to 600 nm. The R-LED 20d generates red light R with the center wavelength of 620 to 630 nm and the wavelength range of 600 to 650 nm.

Figure 3:
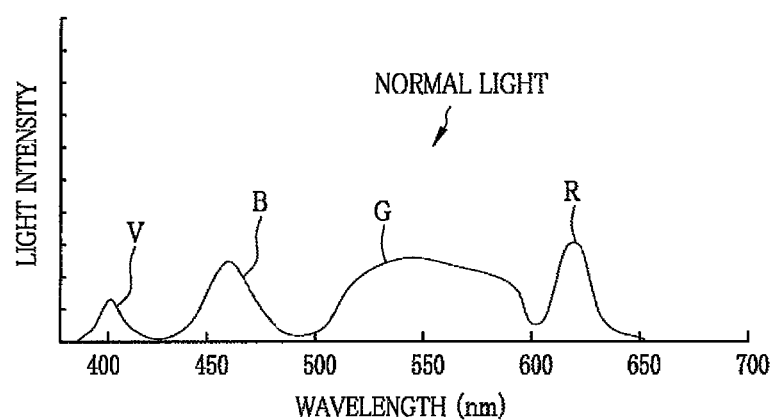
FIG. 3 is a graph illustrating an emission spectrum of normal light.
Figure 4:
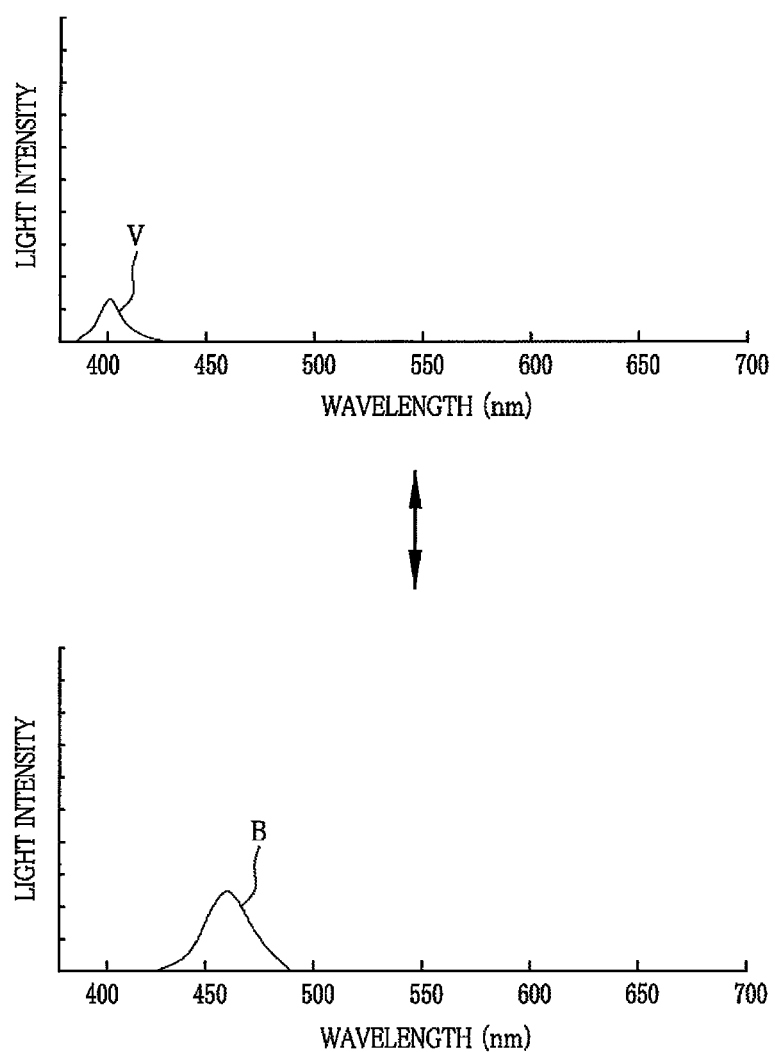
FIG. 4 is a graph illustrating emission spectra of violet light V and blue light B.

In the normal mode, the light source controller 21 turns on all of the V-LED 20a, the B-LED 20b, the G-LED 20c, and the R-LED 20d. As shown in FIG. 3, the optical paths of the light of four colors (the violet light V, the blue light B, the green light G, and the red light R) are coupled through the optical path coupler 23. Thus, the normal light is generated. The normal light is incident on the light guide 41. In the special mode, the V-LED 20a and the B-LED 20b are turned on alternately on a frame basis. As shown in FIG. 4, the violet light V and the blue light B is applied alternately to the observation object on a frame basis. The alternately applied light is incident on the light guide 41 through the optical path coupler 23.

The light guide 41 extends through a universal cord that connects the light source device 14 and the endoscope 12, and transmits the light integrated by the optical path coupler 23 to the distal portion 12d of the endoscope 12. Note that a multimode fiber is used as the light guide 41. For example, a small-diameter fiber cable with the core diameter 105 μm, the clad diameter 125 μm, and the outer diameter φ 0.3 to 0.5 mm (including a protection layer, being a jacket) may be used.

The distal portion 12d of the endoscope 12 has an illumination optical system 30a and an imaging optical system 30b. The illumination optical system 30a has the lighting lens 45, through which the light from the light guide 41 is applied to the observation object. The imaging optical system 30b has an objective lens 46, the zooming lens 47, and an image sensor 48. The light reflected from the observation object is incident on the image sensor 48 through the objective lens 46 and the zooming lens 47. Thereby, a reflection image of the observation object is formed on the image sensor 48.

The image sensor 48 is a color imaging device, which captures the reflection image of the observation object and outputs image signals. It is preferable that the image sensor 48 is a CCD (Charge Coupled Device) image sensor, a CMOS (Complementary Metal-Oxide Semiconductor) image sensor, or the like. The image sensor of the present invention is a color image sensor for obtaining image signals of three colors, R (red), G (green), and B (blue), that is, a so-called RGB image sensor comprising R, G, and B filters in an imaging surface. Here, a pixel with the R filter is referred to as an R pixel. A pixel with the G filter is referred to as a G pixel. A pixel with the B filter is referred to as a B pixel.

Figure 5:
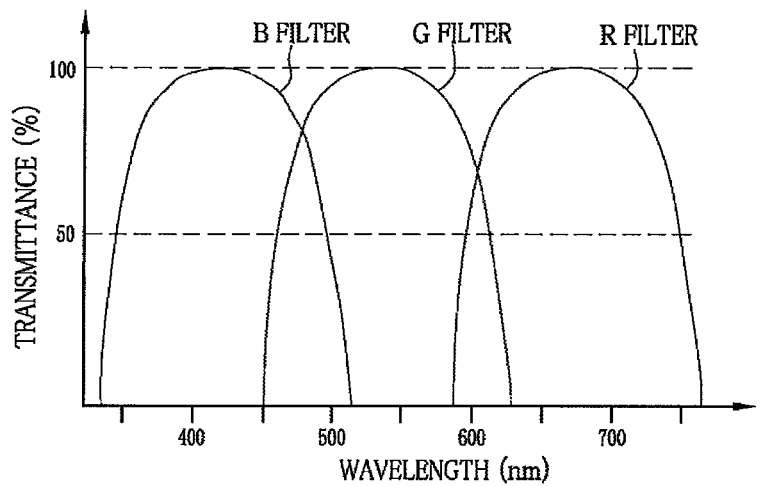
FIG. 5 is a graph illustrating spectral transmittance of B filter, G filter, and R filter.

As shown in FIG. 5, the B filter passes light of 340 to 520 nm. The G filter passes light of 450 to 630 nm. The R filter passes light of 580 to 770 nm. Of the light reflected from the observation object, the violet light V in the wavelength range of 380 to 440 nm and the blue light B in the wavelength range of 440 to 480 nm pass through the B filter. The green light G in the wavelength range of 480 to 600 nm passes through both the B filter and the G filter. The red light in the wavelength range, of 600 to 650 nm passes through the R filter.

Figure 6A:
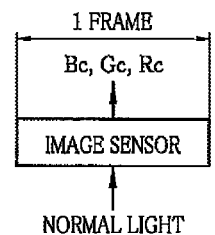
FIG. 6A is an explanatory view illustrating operation of an image sensor in a normal mode.
Figure 6B:
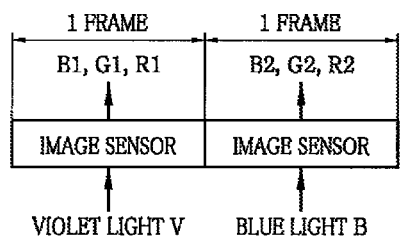
FIG. 6B is an explanatory view illustrating operation of the image sensor in a special mode.

Image signals outputted from the image sensor 48 differ between the normal mode and the special mode. In the normal mode, as shown in FIG. 6A, the normal light is applied to the observation object in each frame, so that a Bc image signal, a Gc image signal, and an Rc image signal, which correspond to the normal light, are outputted from the B pixels, the G pixels, and the R pixels of the image sensor 48, respectively, in each frame. In the special mode, as shown in FIG. 6B, the violet light V and the blue light B are alternately applied on a frame basis. With the application of the violet light V, a B1 image signal, a G1 image signal, and an R1 image signal, which correspond to the violet light V, are outputted from the B pixels, the G pixels, and the R pixels of the image sensor 48, respectively. With the application of the blue light B, a B2 image signal, a G2 image signal, and an R2 image signal, which correspond to the blue light B, are outputted from the B pixels, the G pixels, and the R pixels of the image sensor 48, respectively.

Figure 7:
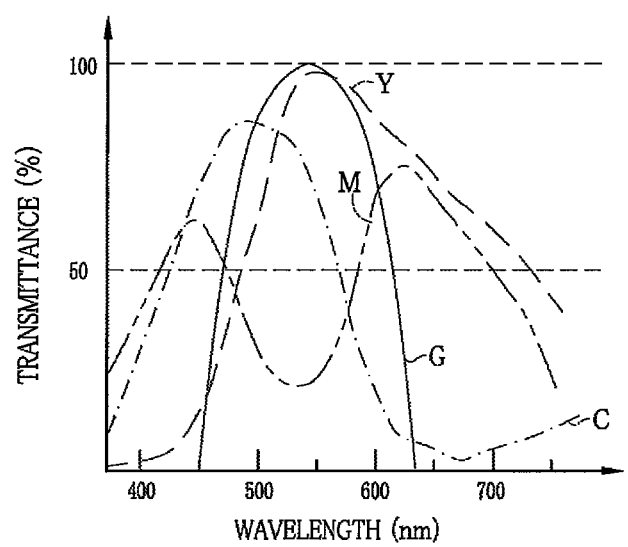
FIG. 7 is a graph illustrating spectral transmittance of a G (green) filter and complementary color filters of C (cyan), M (magenta), and Y (yellow)

Note that the image sensor 48 may be a so-called complementary color image sensor instead of the RGB image sensor. The complementary color image sensor is provided with complementary color filters of C (cyan), M (magenta), Y (yellow), and G (green) with the spectral transmittance shown in FIG. 7, by way of example. In a case where the complementary color image sensor is used, the RGB image signals of three colors are obtained by color conversion of CMYG image signals of four colors. In this case, a color converting means for color-converting the CMYG image signals of four colors into the RGB image signals of three colors is provided to one of the endoscope 12 and the processor device 16.

As shown in FIG. 2, the image signal outputted from the image sensor 48 is transmitted to a CDS/AGC circuit 50. The CDS/AGC circuit 50 performs correlated double sampling (CDS) and automatic gain control (AGC) on the image signal, being an analog signal. An A/D converter 52 converts the image signal, outputted from the CDS/AGC circuit 50, into a digital image signal. The A/D-converted digital image signal is inputted to the processor device 16.

The processor device 16 comprises a receiver 53, a light amount calculator 54, a DSP (digital signal processor) 56, a noise remover 58, an image processing selector 60, a normal-mode image processing unit 62, a special-mode image processing unit 64, and a video signal generator 66. The receiver 53 receives the digital RGB image signals from the endoscope 12. The light amount calculator 54 calculates an exposure amount based on the digital image signal received by the receiver 53, and then calculates a target light amount based on the calculated exposure amount. The light amount calculator 54 calculates a target light amount setting signal, which determines the target light amounts of the respective LEDs 20a to 20d, based on the calculated exposure amount and a light amount ratio between the V-LED 20a, the B-LED 20b, the G-LED 20c, and the R-LED 20d.

For example, in the normal mode, the target light amount of the V-LED 20a is "P×(a/(a+b+c+d))" where "P" denotes the exposure amount calculated by the light amount calculator 54 and the light amount ratio is "V-LED:B-LED:G-LED:R-LED=a:b:c:d". The target light amount of the B-LED 20b is "P×(b/(a+b+c+d))". The target light amount of the G-LED 20c is "P×(c/(a+b+c+d))". The target light amount of the R-LED 20d is "P×(d/(a+b+c+d))". In the special mode, the target light amount of the V-LED 20a is "Q×(m/(m+n))" and the target light amount of the B-LED 20b is "Q×(n/(m+n))", where "Q" denotes the exposure amount calculated by the light amount calculator 54 and the light amount ratio is "V-LED:B-LED=m:n". Note that the light amount ratios are set by the console 19, and differ between the normal mode and the special mode.

The DSP 56 performs gamma correction and a color correction process on the image signal. The noise remover 58 performs a noise removing process (for example, method of moving average or median filter method) on the image signal which has been subjected to the gamma correction and the like in the DSP 56. Thus, noise is removed from the image signal. Then, the image signal is transmitted to the image processing selector 60.

In a case where the observation mode is set to the normal mode by the operation of the mode SW 13a, the image processing selector 60 transmits the Rc image signal, the Gc image signal, and the Bc image signal, which are obtained in the normal mode, to the normal-mode image processing unit 62. In the case of the special mode, the R1 image signal, the G1 image signal, the B1 image signal, the R2 image signal, the G2 image signal, and the B2 image signal, which are obtained in the special mode, are transmitted to the special-mode image processing unit 64.

The normal-mode image processing unit 62 has a normal-mode color converter 68, a normal-mode color enhancer 70, and a normal-mode structure enhancer 72. The normal-mode image processing unit 62 produces the normal image, of an observation object, in actual color of tissue. The normal-mode color converter 68 performs a color conversion process on the Rc image signal, the Gc image signal, and the Bc image signal, and thereby outputs color-converted image signals. The normal-mode color converter 68 then performs a gradation conversion process on the color-converted image signals, and outputs gradation-converted image signals. The normal-mode color enhancer 70 performs various color enhancement processes on the gradation-converted image signals, and thereby outputs color-enhanced image signals. The normal-mode structure enhancer 72 performs a structure enhancement process such as sharpness and edge enhancement on the color-enhanced image signals. The image signals, which have been subjected to the structure enhancement process in the normal-mode structure enhancer 72, are inputted as the normal image to the video signal generator 66.

The special-mode image processing unit 64 has a special-mode color converter 74, a special-mode color enhancer 76, and a special-mode structure display controller 78. The special-mode image processing unit 64 produces the special image in which the most superficial blood vessels, the superficial blood vessels, and the middle-layer blood vessels are distinguished from each other by differences in brightness. The middle-layer blood vessels are located deeper than the superficial blood vessels, and the superficial blood vessels are located deeper than the most superficial blood vessels below a mucosal surface (surface of a mucous membrane). The special-mode color converter 74 performs a color conversion process on a part or the entire of the R1 image signal, the G1 image signal, the B1 image signal, the R2 image signal, the G2 image signal, and the B2 image signal, and thereby outputs color-converted RGB image signals.

In the special mode, the B1 image signal, which is produced by the B pixels detecting the violet light V when the violet light V is applied, and the B2 image signal, which is produced by the B pixels detecting the blue light when the blue light B is applied, contain information related to the observation object such as information about the blood vessels of the observation object. The image signals other than the B1 and B2 signals, namely, the G1 image signal, the R1 image signal, the G2 image signal, and the R2 image signal scarcely contain the information related to the observation object. Hence, in this embodiment, the B1 and B2 image signals are subjected to the color conversion process.

The special-mode color converter 74 then performs a gradation conversion process on the color-converted B1 and B2 image signals, and thereby outputs gradation-converted B1 and B2 image signals. The special-mode color enhancer 76 performs various color enhancement processes on the gradation-converted B1 and B2 image signals. The special-mode structure display controller 78, which will be described in detail below, performs a display control process on color-enhanced B1 and B2 image signals so as to display the most superficial blood vessels, the superficial blood vessels, and the middle-layer blood vessels in a distinguishable manner with different brightness. The B1 and B2 image signals, which have been subjected to the display control process in the special-mode structure display controller 78, are inputted to the video signal generator 66.

Figure 8:
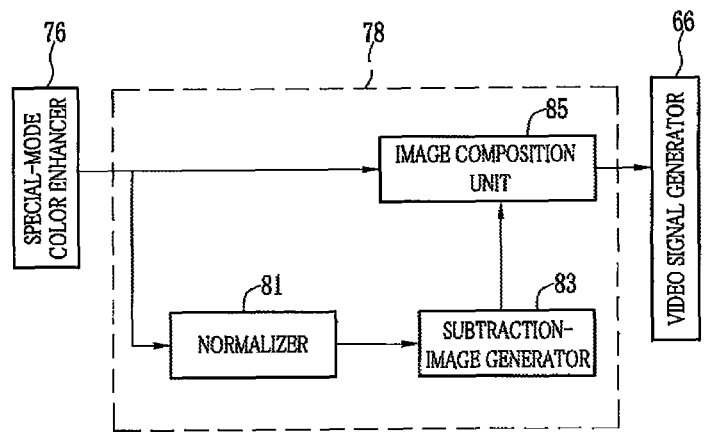
FIG. 8 is a block diagram illustrating a function of a special-mode structure display controller.
Figure 9:
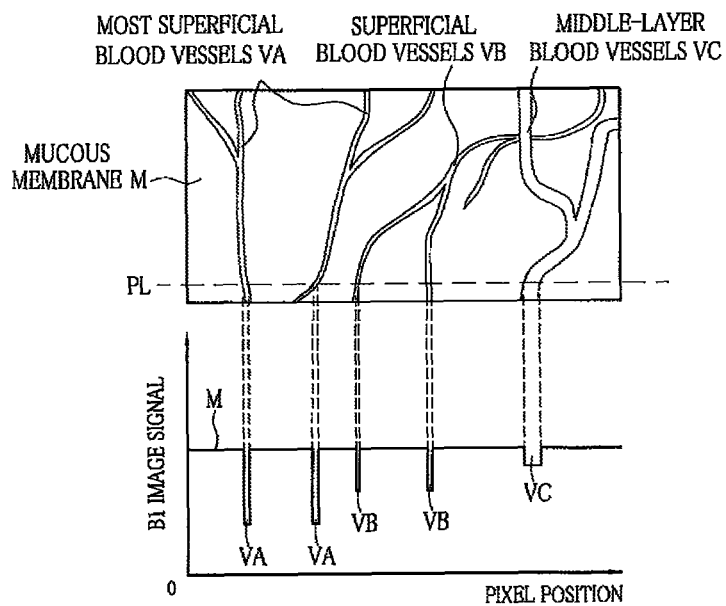
FIG. 9 is an explanatory view illustrating a color-enhanced B1 image signal and signal distribution of the color-enhanced B1 image signal in a predetermined pixel line in the B1 image signal.

As shown in FIG. 8, the special-mode structure display controller 78 comprises a normalizer 81, a subtraction-image generator 83, and an image composition unit 85. The color-enhanced B1 and B2 signals are inputted to the special-mode structure display controller 78. As shown in FIG. 9, as for the color-enhanced B1 image signal (hereinafter simply referred to as the B1 image signal) in a predetermined pixel line PL, each of the most superficial blood vessels VA, the superficial blood vessels VB, and a middle-layer blood vessel VC corresponds to a negative or falling edge with a pixel value lower than that of a mucous membrane M. Of the blood vessels corresponding to the falling edges, the most superficial blood vessel VA has the lowest pixel value. The superficial blood vessel VB has the second lowest pixel value. The middle-layer blood vessel VC has the highest pixel value.

Figure 10:
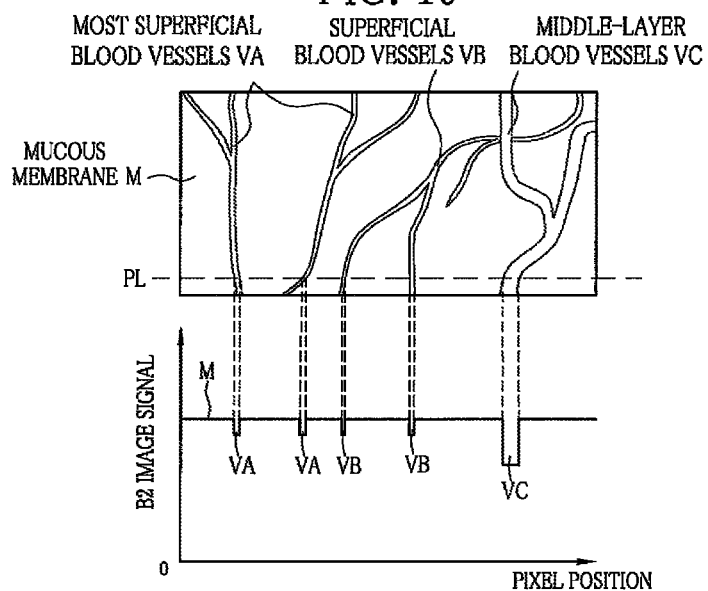
FIG. 10 is an explanatory view illustrating a color-enhanced B2 image signal and signal distribution of the color-enhanced B2 image signal in a predetermined pixel line in the B2 image signal.

As shown in FIG. 10, as for the color-enhanced B2 image signal (hereinafter simply referred to as the B2 image signal) in the predetermined pixel line PL, each of the most superficial blood vessels VA, the superficial blood vessels VB, and the middle-layer blood vessel VC corresponds to a falling edge with a pixel value lower than that of the mucous membrane M, in a manner similar to the B1 image signal. Although the blood vessels correspond to the falling edges, the B2 image signal differs from the B1 image signal in that the pixel value of the most superficial blood vessel VA is substantially the same as that of the superficial blood vessel VB, and each of the pixel values of the most superficial blood vessels VA and the pixel values of the superficial blood vessels VB is higher than the pixel value of the middle-layer blood vessel VC.

The following describes the cause of the signal distribution in the B1 image signal shown in FIG. 9. Since the B1 image signal is obtained during the application of the violet light V, the pixel values corresponding to the blood vessels in the B1 image signal are significantly affected by an amount of light reflected from the blood vessels when the violet light V is applied. Here, the reflectance of the blood vessel corresponding to the violet light V in the wavelength range of 380 to 440 nm differs depending on a depth d of the blood vessel as shown by a result of simulation illustrated in FIG. 11. The depth d of the blood vessel indicates the distance from the mucosal surface to the blood vessel.

Figure 11:
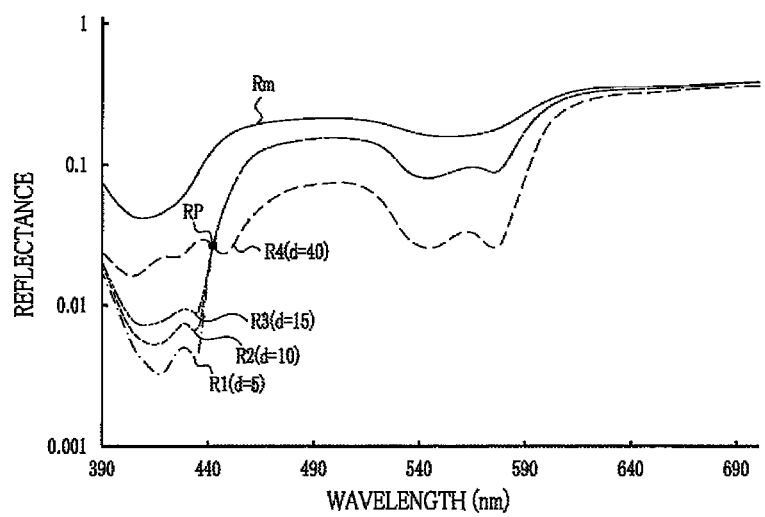
FIG. 11 is a graph illustrating spectral reflectances of a mucous membrane and blood vessels at various depths, which are obtained by simulation.

FIG. 11 shows a reflectance Rm of the mucous membrane M, reflectances R1 to R3 of blood vessels of 10 μm in diameter, and a reflectance R4 of a blood vessel of 40 μm in diameter, under light of predetermined wavelengths. The R1 represents the reflectance of the most superficial blood vessel VA located at the depth d of 5 μm. The R2 and R3 represent the reflectances of the superficial blood vessels VB located at the depths d of 10 μm and 15 μm, respectively. The R4 represents the reflectance of the middle-layer blood vessel VC located at the depth d of 40 μm.

In this embodiment, the most superficial blood vessel VA refers to a blood vessel which has the reflectance R1 and located at the depth of 5 μm. The most superficial blood vessel VA may refer to a blood vessel located at the depth of up to approximately 8 μm from the mucosal surface. The superficial blood vessels VB refer to blood vessels located at the depths d of 10 μm and 15 μm. The superficial blood vessel VB may refer to a blood vessel at the depth d of 8 μm to 20 μm. The middle-layer blood vessel VC refers to a blood vessel located at the depth d of 40 μm. The middle-layer blood vessel VC may refer to a blood vessel located at the depth d of 20 to 45 μm.

The wavelength range (380 to 440 nm) of the violet light V is on the shorter wavelength side than an intersection point RP (close to 440 nm) at which the reflectances of the most superficial blood vessel VA, the superficial blood vessels VB, and the middle-layer blood vessel VC substantially coincide with each other. In the wavelength range 380 to 440 nm, the reflectance decreases in the order of the middle-layer blood vessel VC, the superficial blood vessels VB, and the most superficial blood vessel VA. In other words, the pixel value decreases and the contrast relative to the mucous membrane M increases in the order of the middle-layer blood vessel VC, the superficial blood vessels VB, and the most superficial blood vessel VA. This means that the visible light such as the violet light V of less than or equal to 440 nm has resolving power for depths of blood vessels.

The following is the cause of the signal distribution in the B2 image signal shown in FIG. 10. Since the B2 image signal is obtained when the blue light B is applied, the pixel value which corresponds to the blood vessel in the B2 image signal is significantly affected by an amount of light reflected by the blood vessel when the blue light B is applied. As shown in FIG. 11, the wavelength range (440 to 480 nm) of the blue light B is on a longer wavelength side than the intersection point RP. In the wavelength range of 440 to 480 nm, the reflectance of the middle-layer blood vessel VC is smaller than each of the reflectances of the most superficial blood vessel VA and the superficial blood vessels VB. In other words, as compared with the case of the B1 image signal, the magnitude relationship between the reflectance of the middle-layer blood vessel VC and the reflectances of the most superficial and superficial blood vessels VA and VB is reversed.

In the wavelength range (440 to 480 nm) of the blue light. B, the reflectance of the most superficial blood vessel VA is substantially the same as the reflectances of the superficial blood vessels VB. The pixel value does not change even if the depth d of the blood vessel varies within a range (from 5 to 15 μm), which includes the depths d of the superficial blood vessels VB. This means that the light exceeding the wavelength of 440 nm such as the blue light B does not have the resolving power for depths of the blood vessels in a case where the blood vessels are located at the depth d in the range of 5 to 15 μm.

As described above, in the B2 image signal, the pixel values of the most superficial and superficial blood vessels VA and VB, which are located at the depths d within the range of 5 to 15 μm, are substantially the same. The pixel value of the middle-layer blood vessel VC at the depth d deeper than 15 μm is smaller than each of the pixel value of the most superficial blood vessel VA and the pixel value of the superficial blood vessel VB.

Figure 12:
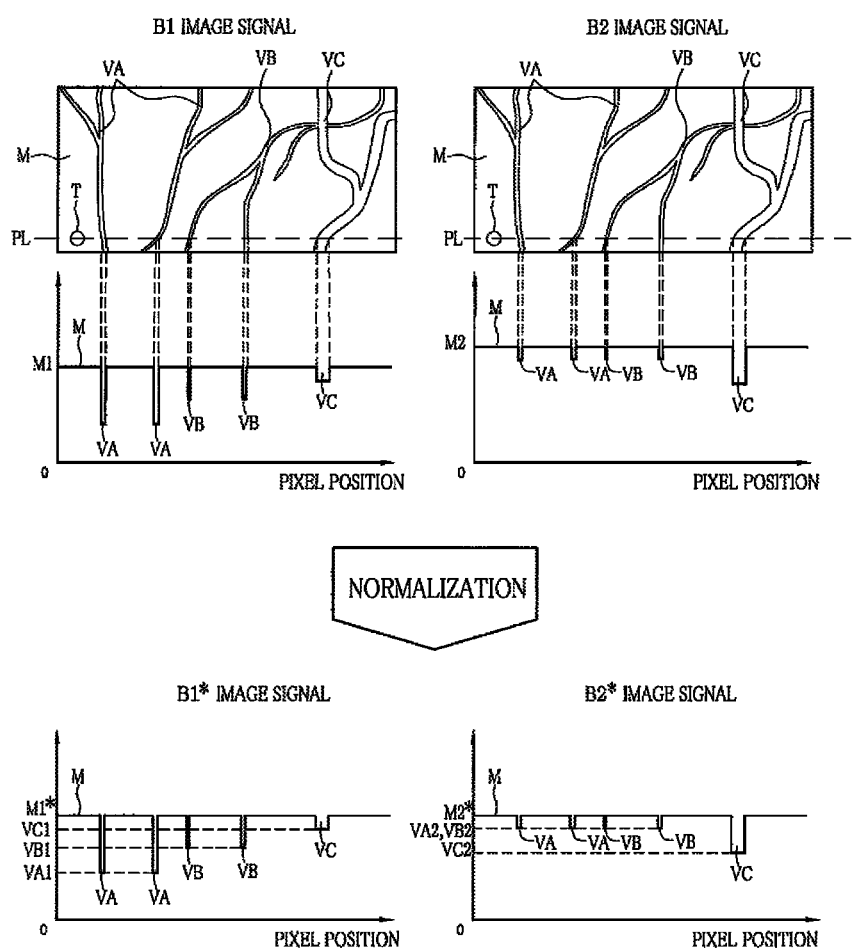
FIG. 12 is an explanatory view illustrating normalization of the B1 and B2 image signals.

The normalizer 81 makes the pixel value of the mucous membrane M in the B1 image signal equivalent to that of the mucous membrane M in the B2 image signal and thereby normalizes the B1 and B2 image signals. As shown in FIG. 12, the normalizer 81 extracts the pixels, corresponding to the mucous membranes M, at the same positions T in the B1 and B2 image signals, respectively. Pixel values M1 and M2 of the extracted pixels, which correspond to the mucous membrane M, are obtained. A value which is obtained by dividing the normalization coefficient PM by the pixel value M1 of the mucous membrane is multiplied by the pixel value of each pixel of the B1 image signal, and thereby a normalized B1* image signal is obtained (B1*=B1×(PM/M1). In a similar manner, a value which is obtained by dividing the normalization coefficient PM by the pixel value M2 of the mucous membrane is multiplied by the pixel value of each pixel of the B2 image signal, and thereby a normalized B2* image signal is obtained (B2*=B2×(PM/M2). A pixel value M1* of the mucous membrane M in the normalized B1* image signal is equivalent to a pixel value M2* of the mucous membrane M in the normalized B2* image signal.

Note that the pixel value of the mucous membrane M is calculated every time the B1 and B2 image signals are obtained. Instead, in a case where the pixel values M1 and M2 of the mucous membrane M have known quantities, predetermined fixed values may be used for M1 and M2. In this case, however, it is necessary to adjust the predetermined fixed values based on a level of the light amount of the illumination light or a level of the exposure amount calculated by the light amount calculator 54.

The subtraction-image generator 83 subtracts the pixel value of the normalized B2* image signal from the pixel value of the normalized B1* image signal, and thereby produces a subtraction image D (D=B1*−B2*). The pixel value M1* of the mucous membrane in the B1* image signal is substantially the same as the pixel value M2* of the mucous membrane in the B2* image signal (M1*=M2*), so that the value of the mucous membrane M in the subtraction image D is substantially "0" (M1*−M2*=0) as shown by a subtraction process in FIG. 13. Note that the subtraction-image generator 83 may subtract the B2* image signal from the B1* image signal (and vice versa) to produce the subtraction image.

A pixel value VA1 of the most superficial blood vessel VA in the B1* image signal is smaller than a pixel value VA2 of the most superficial blood vessel VA in the B2* image signal. A pixel value VB1 of the superficial blood vessel VB in the B1* image signal is smaller than a pixel value VB2 of the superficial blood vessel VB in the B2* image signal (VA1<VA2, VB1<VB2). Accordingly, in the subtraction image D, each of the value of the most superficial blood vessel VA and the value of the superficial blood vessel VB is negative and an absolute value of the most superficial blood vessel VA is greater than an absolute value of the superficial blood vessel VB (VA1−VA2<0, VB1−VB2<0, |VA1−VA2|>|VB1−VB2|). A pixel value VC1 of the middle-layer blood vessel VC in the B1* image signal is greater than a pixel value VC2 of the middle-layer blood vessel VC in the B2* image signal (VC1>VC2). Accordingly, the value of the middle-layer blood vessel VC in the subtraction image D is positive (VC1−VC2>0).

The subtraction-image generator 83 multiplies each pixel value of the subtraction image by an adjustment factor α, and thereby produces a subtraction image D*. The adjustment factor α is adjusted in accordance with the pixel value of the subtraction image, so that the most superficial blood vessels VA, the superficial blood vessels VB, and the middle-layer blood vessels VC are surely distinguished from each other in the displayed image in the case where the subtraction image D is added to the B1 image signal in the image composition unit 85. In this embodiment, the middle-layer blood vessels VC correspond to positive or rising edges so as to display the most superficial blood vessels VA, the superficial blood vessels VB, and the middle-layer blood vessels VC in a distinguishable manner. The adjustment factor α is adjusted to make the absolute value of the middle-layer blood vessel VC in the subtraction image greater than the absolute value of the middle-layer blood vessel VC in the B1 image signal.

The image composition unit 85 superimposes the subtraction image D* on the B1 image signal, and thereby produces the special image. Here, the image composition unit 85 adds the subtraction image D* to the B1 image signal, and thereby produces the special image. Instead, image subtraction between the B1 image signal and the subtraction image D* may be made to produce the special image. Alternatively, the subtraction image D* may be added to or subtracted from the B2 image to produce the special image.

Figure 14:
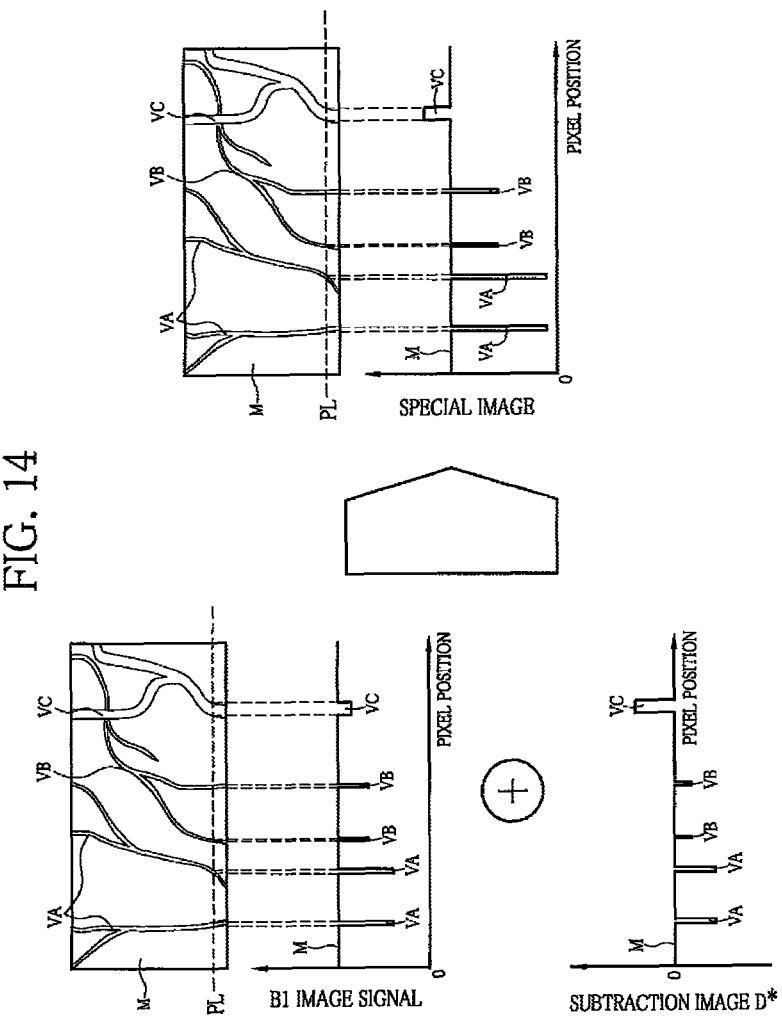
FIG. 14 is an explanatory view illustrating a method for producing a special image.

As shown in FIG. 14, the pixel value of the most superficial blood vessel VA which corresponds to the falling edge in the B1 image signal is added to the value of the most superficial blood vessel VA which corresponds to the falling edge in the subtraction image D*, and thereby the most superficial blood vessel VA of the special image is obtained. The pixel value of the superficial blood vessel VB which corresponds to the falling edge in the B1 image signal is added to the value of the superficial blood vessel VB which corresponds to the falling edge in the subtraction image D*, and thereby the superficial blood vessel VB of the special image is obtained. Accordingly, the most superficial blood vessels VA and the superficial blood vessels VB maintain the falling edges in the special image. As for the middle-layer blood vessel VC, the pixel value of the middle-layer blood vessel VC which corresponds to the falling edge in the B1 image signal is added to the value of the middle-layer blood vessel VC which corresponds to the rising edge in the subtraction image D*, and thereby the middle-layer blood vessel VC of the special image is obtained. Accordingly, the middle-layer blood vessel VC corresponds to the rising edge in the special image. Thus, the most superficial blood vessels VA, the superficial blood vessels VB, and the middle-layer blood vessel VC are distinguished from each other in the displayed special image.

As for the most superficial blood vessels VA and the superficial blood vessels VB in the special image, the subtraction image D*, which satisfies the relationships VA1−VA2<0, VB1−VB2<0, and |VA1−VA2|>|VB1−VB2|, is added to B1 image signal. Thereby, the contrast of the most superficial blood vessels VA and the contrast of the superficial blood vessels VB are improved. The contrast of the most superficial blood vessels VA is greater than that of the superficial blood vessels VB. Thus, the most superficial blood vessels VA and the superficial blood vessels VB are distinguished from each other by the difference in contrast. Since the value of the mucous membrane M in the subtraction image D* is approximately "0", the mucous membrane M is not enhanced even if the subtraction image D* is added to the B1 image signal. Thus, the visibility of each of the blood vessels VA, VB, and VC is improved without enhancing the mucous membrane.

The video signal generator 66 converts the normal image, which is inputted from the normal-mode image processing unit 62, or the special image, which is inputted from the special-mode image processing unit 64, into a video signal for displaying the normal image or the special image on the monitor 18. Based on the video signal after the conversion, the monitor 18 displays the normal image in the normal mode and the special image in the special mode. Note that, in this example, the special image consists of the added image in which the subtraction image D* is added to the B1 image signal. In addition, the B2 image signal may be added to the added image, and then displayed on the monitor 18. In this case, it is preferable to assign the added image to the B and G channels of the monitor 18, and the B2 image signal to the R channel of the monitor 18.

Figure 15:
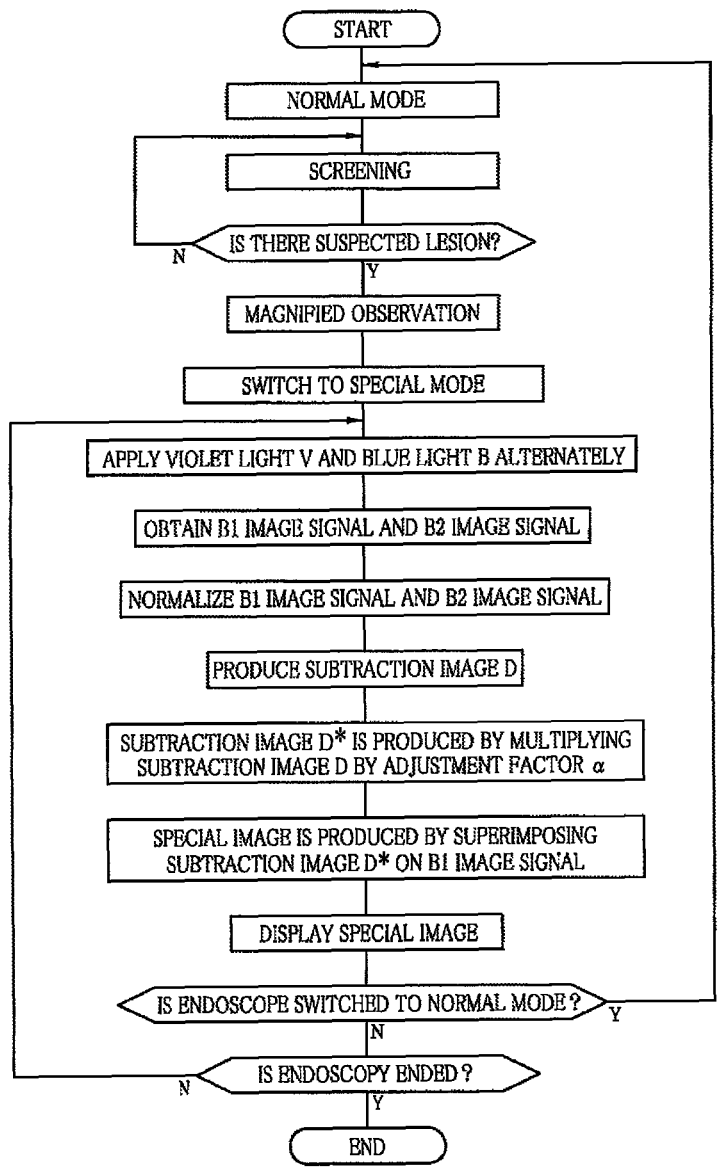
FIG. 15 is a flow chart illustrating a procedure of the present invention.

Next, referring to a flow chart in FIG. 15, an operation of the present invention is described. First, in the normal mode, screening is performed from distant view (in a zoomed-out state). In a case where a body part (suspected lesion) suspected of being a lesion, such as a brownish area or redness, is detected during the screening, the zoom control unit 13b is operated to magnify the display of the suspected lesion. Thus, magnified observation is performed. At this time, the mode SW 13a is operated to switch the observation mode to the special mode.

When the observation mode is switched to the special mode by operating the mode SW 13a, the V-LED 20a and the B-LED 20b are turned on alternately. Thereby, the violet light V and the blue light B is applied alternately to the observation object. The image sensor 48 captures an image of the observation object under the violet light V and an image of the observation object under the blue light B. When the violet light V is applied, the image sensor 48 outputs the R1, G1, and B1 image signals. When the blue light B is applied, the image sensor 48 outputs the R2, G2, and B2 image signals.

Figure 16:
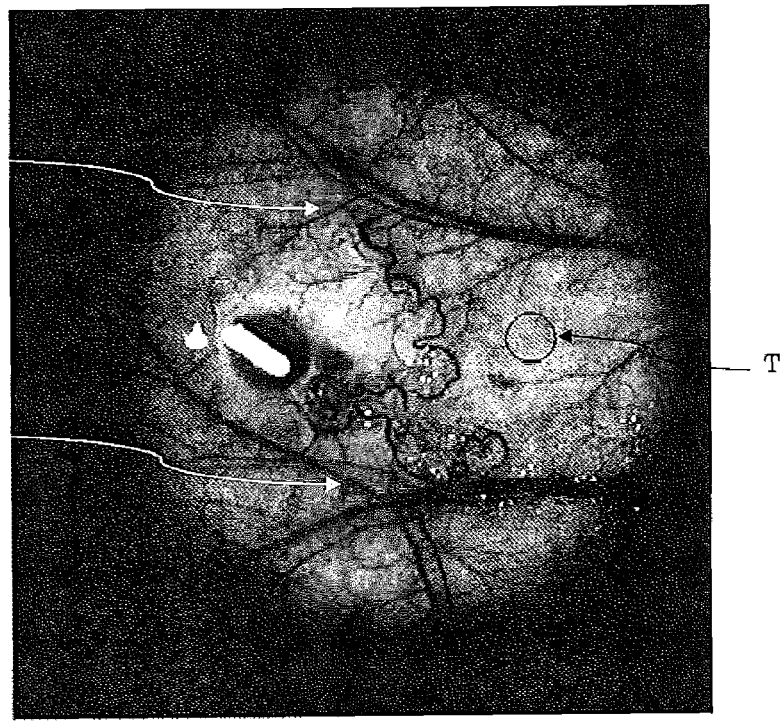
FIG. 16 is an example of an image based on the B1 image signal.
Figure 17:
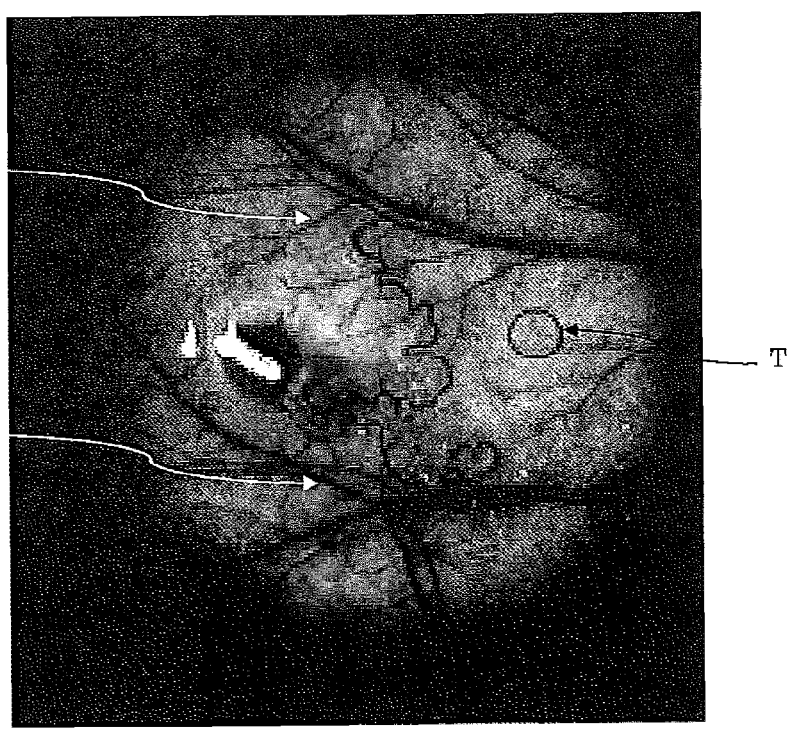
FIG. 17 is an example of an image based on the B2 image signal.
Figure 18:
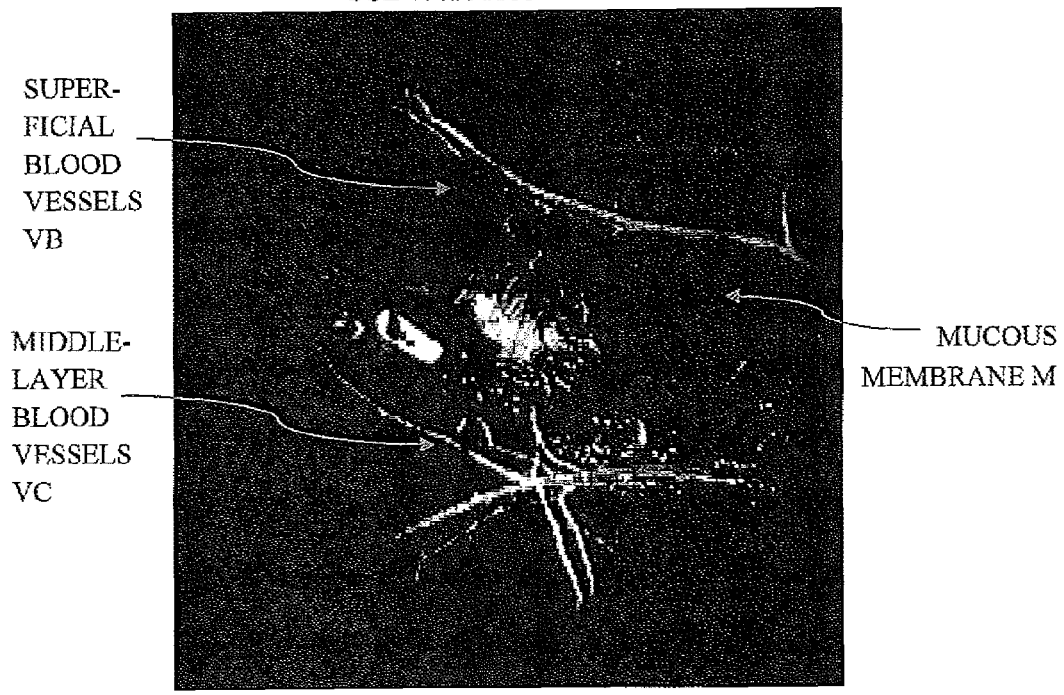
FIG. 18 is an example of an image based on a subtraction image D.

The special image is produced based on the B1 image signal and the B2 image signal, of the image signals obtained in the special mode. As for the B1 image signal shown in FIG. 16, the superficial blood vessels VB and the middle-layer blood vessels VC correspond to falling edges which are darker than the mucous membrane M. As for the B2 image signal shown in FIG. 17, the superficial blood vessels VB and the middle-layer blood vessels VC also correspond to falling edges. First, the pixels, corresponding to the mucous membrane M, located at the same positions T in the B1 and B2 image signals are extracted, respectively, and the pixel values of the extracted pixels that correspond to the mucous membrane M are obtained. Based on the pixel values corresponding to the mucous membrane M, the B1 and B2 image signals are normalized such that the pixel values corresponding to the mucous membrane M in the B1 and B2 image signals are the same. The normalized B2 image signal is subtracted from the normalized B1 image signal. Thereby, the subtraction image D shown in FIG. 18 is obtained. In the subtraction image D, the value corresponding to the mucous membrane M is approximately "0". The superficial blood vessel VB corresponds to a falling edge (negative edge) with a value smaller than the value of the mucous membrane M. The middle-layer blood vessel VC corresponds to a rising edge (positive edge) with a value greater than the value of the mucous membrane M.

Figure 19:
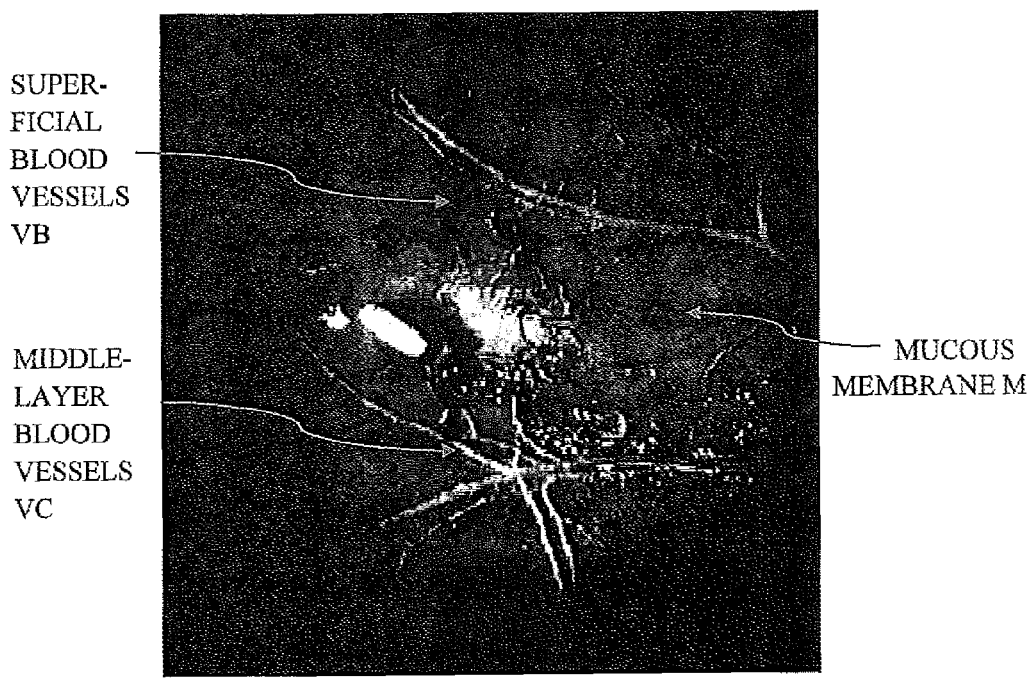
FIG. 19 is an example of the special image.

Then, the subtraction image D is multiplied by the adjustment factor α, and thereby the subtraction image D* is obtained. The subtraction image D* is added to the B1 image signal. Thus, the special image shown in FIG. 19 is produced. In the special image, the superficial blood vessels VB correspond to the falling edges, while the middle-layer blood vessels VC correspond to the rising edges. Accordingly, the superficial blood vessels VB and the middle-layer blood vessels VC are distinguished from each other in the displayed special image. In FIG. 19, the superficial blood vessels VB, which correspond to the falling edges, are displayed in black, while the middle-layer blood vessels VC, which correspond to the rising edges, are displayed in white. Note that the most superficial blood vessels VA are not illustrated in FIGS. 16 to 19. In the special image, the contrast of the most superficial blood vessels VA is greater than the contrast of the superficial blood vessels VB, so that the most superficial blood vessels VA are distinguished from the superficial blood vessels VB by the difference in contrast.

(Second Embodiment)

In the first embodiment, the image signals necessary for each observation mode are obtained simultaneously with the color image sensor. In a second embodiment, image signals necessary for each observation mode are obtained sequentially with a monochrome image sensor instead.

Figure 20:
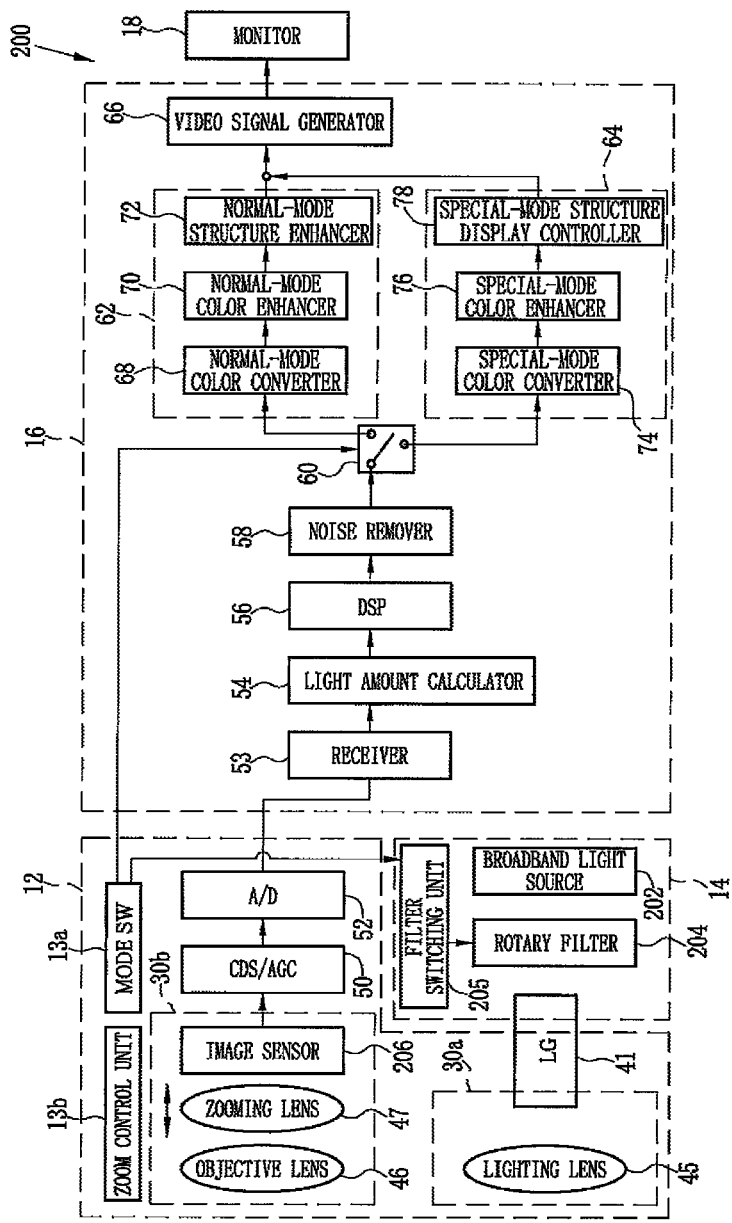
FIG. 20 is a block diagram illustrating a function of an endoscope system of a second embodiment.

As shown in FIG. 20, the light source device 14 of a frame sequential type endoscope system 200 is provided with a broadband light source 202, a rotary filter 204, and a filter switching unit 205, instead of the V-LED 20a and the like. The imaging optical system 30b is provided with a monochrome image sensor 206 with no color filter, instead of the color image sensor 48. The rest of the parts correspond to those of the endoscope system 10 of the first embodiment.

The broadband light source 202 is a xenon lamp, a white LED, or the like, which applies white light with a wavelength range from blue to red regions. The rotary filter 204 comprises a normal mode filter 208, which is located on the inner side, and a special mode filter 209, which is located on the outer side (see FIG. 21). The filter switching unit 205 moves the rotary filter 204 in a radial direction. The filter switching unit 205 inserts the normal mode filter 208 of the rotary filter 204 into an optical path of the white light in a case where the mode SW 13a is operated to set the observation mode to the normal mode. The filter switching unit 205 inserts the special mode filter 209 of the rotary filter 204 into the optical path of the white light in a case where the mode SW 13a is operated to set the observation mode to the special mode.

Figure 21:
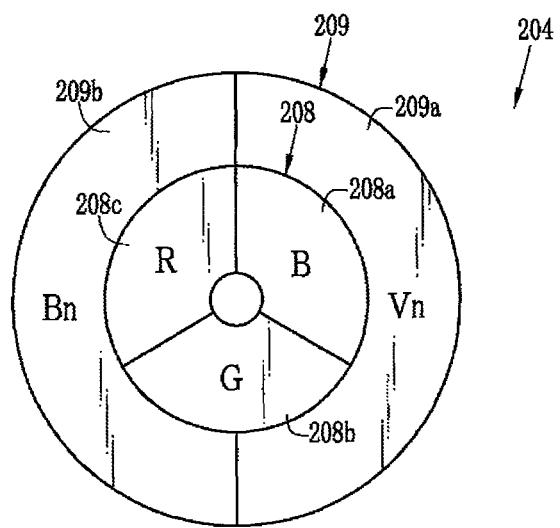
FIG. 21 is a plan view of a rotary filter.

As shown in FIG. 21, the normal mode filter 208 is provided with a B filter 208a, a G filter 208b, and an R filter 208c in a circumferential direction. The B filter 208a passes broadband blue light of the white light. The G filter 208b passes broadband green light of the white light. The R filter 208c passes broadband red light of the white light. In the normal mode, the broadband blue light, the broadband green light, and the broadband red light are applied sequentially to the observation object when the rotary filter 204 is rotated.

The special mode filter 209 is provided with a Vn filter 209a and a Bn filter 209b in a circumferential direction. The Vn filter 209a passes the violet light V, with the wavelength range of 380 to 440 nm and the center wavelength 405 nm, of the white light. The Bn filter 209b passes the blue light B, with the wavelength range of 440 to 480 nm, of the white light. In the special mode, the violet light V and the blue light B are applied alternately to the observation object when the rotary filter 204 is rotated.

In the frame sequential type endoscope system 200, in the normal mode, an image of the observation object is captured with the monochrome image sensor 206 every time each of the blue light, the green light, and the red light is applied to the observation object. Thereby, the RGB image signals of three colors are obtained. Based on the RGB image signals, the normal image is produced in a manner similar to the first embodiment. In the special mode, an image of the observation object is captured with the monochrome image sensor 206 every time each of the violet light V and the blue light B is applied to the observation object. Thereby, a Vn image signal and a Bn image signal are obtained. The special image is produced based on the Vn image signal and the Bn image signal in a manner similar to the first embodiment. Note that the Vn image signal corresponds to the B1 image signal of the first embodiment. The Bn image signal corresponds to the B2 image signal of the first embodiment.

Figure 22:
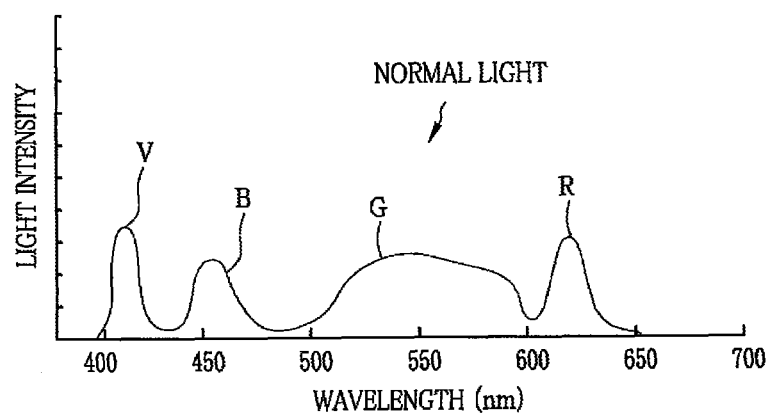
FIG. 22 is a graph illustrating an emission spectrum of normal light which is different from the normal light in FIG. 3.

In the first embodiment, the four colors of light having the emission spectra shown in FIGS. 3 and 4 are used. Note that the emission spectra are not limited to these. For example, as shown in FIG. 22, the green light G and the red light R have the spectra similar to those of the first embodiment. The violet light V, on the other hand, may have a wavelength range on a somewhat long wavelength side, with the center wavelength of 410 to 415 nm. The blue light B may have a wavelength range on a somewhat short wavelength side, with the center wavelength of 445 to 460 nm. In this case, the upper limit of the wavelength range of the violet light V needs to be on the shorter wavelength side than the intersection point RP (440 nm) in FIG. 11 and the lower limit of the wavelength range of the blue light B needs to be on the longer wavelength side than the intersection point RP (440 nm) so as to produce the subtraction image D in which the most superficial blood vessels VA and the superficial blood vessels VB correspond to the falling edges and the middle-layer blood vessels VC correspond to the rising edges.

Note that, in the above embodiments, the present invention is implemented while a diagnosis is made using the endoscope. The present invention is not limited to this. The present invention may be implemented based on an endoscopic image recorded in a storage unit of the endoscope system, after the diagnosis using the endoscope. Furthermore, the present invention may be implemented based on an image captured with a capsule endoscope.

Various changes and modifications are possible in the present invention and may be understood to be within the present invention.

What is claimed is:

1. An endoscope system comprising:
    a light source unit for sequentially applying first illumination light and second illumination light to an observation object, the first illumination light having a wavelength range in which a reflectance of a first blood vessel located at a specific depth is smaller than a reflectance of a second blood vessel located at a depth deeper than the specific depth, the second illumination light having a wavelength range in which the reflectance of the first blood vessel is greater than the reflectance of the second blood vessel;
    an image sensor for imaging the observation object under the first illumination light and thereby outputting a first image and imaging the observation object under the second illumination light and thereby outputting a second image, wherein in the first image, the first and second blood vessels correspond to a negative edge with a value smaller than a value of the mucous membrane of the observation object and the first blood vessel has a value smaller than a value of the second blood vessel, and in the second image, the first and second blood vessels correspond to the negative edge and the second blood vessel has a value smaller than a value of the first blood vessel;
    a normalizer for normalizing the first image and the second image to make brightness of the mucous membrane in the first image equivalent to brightness of the mucous membrane in the second image;
    a subtraction-image generator for producing a subtraction image through a subtraction process between normalized first and second images, wherein in the subtraction image, one of the first and second blood vessels corresponds to the negative edge and the other of the first and second blood vessels corresponds to a positive edge with a value greater than the value of the mucous membrane; and
    an image composition unit for producing a special image through superimposing the subtraction image on at least one of the first and second images, one of the first and second blood vessels corresponding to the negative edge in the special image, the other of the first and second blood vessels corresponding to the positive edge in the special image.

2. The endoscope system according to claim 1, wherein the subtraction-image generator produces the subtraction image in which the first blood vessel corresponds to the negative edge and the second blood vessel corresponds to the positive edge, and
    the image composition unit adds a value of the first blood vessel which corresponds to the negative edge in the subtraction image to a value of the first blood vessel which corresponds the negative edge in the first or second image, and adds a value of the second blood vessel which corresponds to the positive edge in the subtraction image to a value of the second blood vessel which corresponds to the negative edge in the first or second image, and thereby produces the special image in which the first blood vessel corresponds to the negative edge and the second blood vessel corresponds to the positive edge.

3. The endoscope system according to claim 1, wherein a value of the mucous membrane in the subtraction image is "0".

4. The endoscope system according to claim 1, wherein the normalizer obtains pixel values of the mucous membrane at the same positions in the first and second images, respectively, and normalizes the first and second images based on the pixel values of the mucous membrane.

5. The endoscope system according to claim 1, wherein the normalizer normalizes the first and second images based on pixel values of the mucous membrane, and the pixel values of the mucous membrane are adjusted in accordance with an amount of the first or second illumination light.

6. The endoscope system according to claim 1, wherein the subtraction image is multiplied by an adjustment factor to make one of the first and second blood vessels correspond to the positive edge in the special image.

7. The endoscope system according to claim 1, wherein a reflectance of a third blood vessel, which is located shallower than the first blood vessel, is smaller than the reflectance of the first blood vessel in the wavelength range of the first illumination light, and contrast of the third blood vessel is greater than contrast of the first blood vessel in the special image.

8. The endoscope system according to claim 7, wherein in the first image, the first to third blood vessels correspond to the negative edge and the third blood vessel has a value smaller than a value of the second blood vessel, and in the second image, the third blood vessel corresponds to the negative edge and the second blood vessel has a value smaller than a value of the third blood vessel, and the subtraction-image generator produces the subtraction image in which the first and third blood vessels correspond to the negative edge and the second blood vessel corresponds to the positive edge, and the image composition unit adds a value of the first blood vessel which corresponds to the negative edge in the subtraction image to a value of the first blood vessel which corresponds to the negative edge in the first or second image, adds a value of the third blood vessel which corresponds to the negative edge in the subtraction image to a value of the third blood vessel which corresponds to the negative edge in the first or second image, and adds a value of the second blood vessel which corresponds to the positive edge in the subtraction image to a value of the second blood vessel which corresponds to the negative edge in the first or second image, and thereby produces the special image in which the first and third blood vessels correspond to the negative edge and the second blood vessel corresponds to the positive edge.

9. The endoscope system according to claim 1, wherein the first illumination light has the wavelength range of 380 to 440 nm, and the second illumination light has the wavelength range of 440 to 480 nm.

10. The endoscope system according to claim 1, wherein the light source unit has a first LED for emitting the first illumination light and a second LED for emitting the second illumination light.

11. A processor device of an endoscope system comprising a light source unit and an image sensor, the light source unit sequentially applying first illumination light and second illumination light to an observation object, the first illumination light having a wavelength range in which a reflectance of a first blood vessel located at a specific depth is smaller than a reflectance of a second blood vessel located at a depth deeper than the specific depth, the second illumination light having a wavelength range in which the reflectance of the first blood vessel is greater than the reflectance of the second blood vessel; the image sensor imaging the observation object under the first illumination light and thereby outputting a first image and imaging the observation object under the second illumination light and thereby outputting a second image, wherein in the first image, the first and second blood vessels correspond to a negative edge with a value smaller than a value of the mucous membrane of the observation object and the first blood vessel has a value smaller than a value of the second blood vessel, and in the second image, the first and second blood vessels correspond to the negative edge and the second blood vessel has a value smaller than a value of the first blood vessel, the processor device comprising:

a receiver for receiving the first and second images;

a normalizer for normalizing the first and second images to make brightness of the mucous membrane in the first image equivalent to brightness of the mucous membrane in the second image;

a subtraction-image generator for producing a subtraction image through a subtraction process between normalized first and second images, wherein in the subtraction image, one of the first and second blood vessels corresponds to the negative edge and the other of the first and second blood vessels corresponds to a positive edge with a value greater than the value of the mucous membrane; and an image composition unit for producing a special image through superimposing the subtraction image on at least one of the first and second images, one of the first and second blood vessels corresponding to the negative edge in the special image, the other of the first and second blood vessels corresponding to the positive edge in the special image.

12. A method for operating an endoscope system comprising the steps of:

sequentially applying first illumination light and second illumination light to an observation object from a light source unit, the first illumination light having a wavelength range in which a reflectance of a first blood vessel located at a specific depth is smaller than a reflectance of a second blood vessel located at a depth deeper than the specific depth, the second illumination light having a wavelength range in which the reflectance of the first blood vessel is greater than the reflectance of the second blood vessel;

imaging the observation object under the first illumination light and thereby outputting a first image and imaging the observation object under the second illumination light and thereby outputting a second image, wherein in the first image, the first and second blood vessels correspond to a negative edge with a value smaller than a value of the mucous membrane of the observation object and the first blood vessel has a value smaller than a value of the second blood vessel, and in the second image, the first and second blood vessels correspond to the negative edge and the second blood vessel has a value smaller than a value of the first blood vessel, with an image sensor;

normalizing the first and second images with a normalizer, to make brightness of the mucous membrane in the first image equivalent to brightness of the mucous membrane in the second image;

producing a subtraction image through a subtraction process between normalized first and second images, wherein in the subtraction image, one of the first and second blood vessels corresponds to the negative edge and the other of the first and second blood vessels corresponds to a positive edge with a value greater than the value of the mucous membrane, with a subtraction-image generator; and producing a special image through superimposing the subtraction image on at least one of the first and second images with an image composition unit, one of the first and second blood vessels corresponding to the negative edge in the special image, the other of the first and second blood vessels corresponding to the positive edge in the special image.

13. An endoscope system comprising:

a light source unit for sequentially applying first illumination light and second illumination light to an observation object, the first illumination light having a wavelength range in which a reflectance of a first blood vessel located at a specific depth is smaller than a reflectance of a second blood vessel located at a depth deeper than the specific depth, the second illumination light having a wavelength range in which the reflectance of the first blood vessel is greater than the reflectance of the second blood vessel;

an image sensor for imaging the observation object under the first illumination light and thereby outputting a first image and imaging the observation object under the second illumination light and thereby outputting a second image;

a normalizer for normalizing the first image and the second image to make brightness of mucous membrane of the observation object in the first image equivalent to brightness of the mucous membrane of the observation object in the second image;

a subtraction-image generator for producing a subtraction image through a subtraction process between normalized first and second images, wherein in the subtraction image, the image of the first blood vessel corresponds to a negative edge with a value smaller than a value of the mucous membrane, and the image of the second blood vessel corresponds to a positive edge with a value larger than a value of the mucous membrane; and an image composition unit for producing a special image through superimposing the subtraction image on at least one of the first and second images, one of the first and second blood vessels corresponding to the negative edge in the special image, the other of the first and second blood vessels corresponding to the positive edge in the special image.

* * * * *